(12) United States Patent
Lynn

(10) Patent No.: US 6,689,109 B2
(45) Date of Patent: Feb. 10, 2004

(54) POSITIVE FLOW GENERATOR FOR INDWELLING MEDICAL FLUID SYSTEMS

(76) Inventor: Lawrence A. Lynn, 862 Curleys Ct., Worthington, OH (US) 43235

( * ) Notice: Subject to any disclaimer, the term of this patent is extended or adjusted under 35 U.S.C. 154(b) by 0 days.

(21) Appl. No.: 09/846,367

(22) Filed: May 2, 2001

(65) Prior Publication Data

US 2001/0039403 A1 Nov. 8, 2001

Related U.S. Application Data

(60) Provisional application No. 60/201,311, filed on May 2, 2000.

(51) Int. Cl.[7] ............................................... A61M 5/00
(52) U.S. Cl. ..................................................... 604/250
(58) Field of Search .......................... 604/30, 34, 169, 604/236, 246, 250, 256, 80–85, 86, 174

(56) References Cited

U.S. PATENT DOCUMENTS

| | | | |
|---|---|---|---|
| 3,802,463 A | | 4/1974 | Dabney |
| 4,257,416 A | * | 3/1981 | Prager .......................... 128/214 |
| 4,364,383 A | * | 12/1982 | Vcelka ........................ 128/214 |
| 4,453,295 A | * | 6/1984 | Laszczower ................. 251/10 |
| 4,869,721 A | | 9/1989 | Karpisek |
| 5,423,769 A | * | 6/1995 | Jonkman et al. ............ 604/250 |
| 5,474,544 A | | 12/1995 | Lynn |
| 6,048,335 A | | 4/2000 | Mayer |
| 6,234,448 B1 | | 5/2001 | Porat |
| 6,428,520 B1 | | 8/2002 | Lopez et al. |
| 6,485,473 B1 | | 11/2002 | Lynn |

OTHER PUBLICATIONS

Clamps and Clips Illustrations; pp. 48/01–55/01; http://www.qosina.com/pdf/sections/ClampsandClips.pdf.

* cited by examiner

*Primary Examiner*—Manuel Mendez
(74) *Attorney, Agent, or Firm*—Nixon & Vanderhye PC

(57) ABSTRACT

A positive pressure generator is provided proximal the valve or septum of a vascular catheter for inducing sufficient positive pressure in the lumen or fluid path of the catheter so that a sufficient portion of the fluid at the tip of the catheter is forced into the blood vessel after the cannula or needle has been removed from the hub so that any blood in the tip is displaced back into the vessel or is sufficiently diluted such that clotting within the lumen adjacent the tip is substantially mitigated. The positive pressure generator is preferably comprised of a flexible tube or cavity which has a variable internal volume and which is configured to have a first stable configuration with a first internal fluid volume and a second stable configuration with a smaller internal fluid volume.

35 Claims, 2 Drawing Sheets

POSITIVE FLOW GENERATOR FOR INDWELLING MEDICAL FLUID SYSTEMS

This application claims the benefit of U.S. Provisional Application No. 60/201,311, which was filed May 2, 2000. The disclosure of which is incorporated herein by this reference.

BACKGROUND AND SUMMARY OF THE INVENTION

This invention relates to vascular catheters and in particular closed catheters for insertion into veins of patients especially those used for long term catheterization.

The terminal or hub of vascular catheters is generally sealed by a valve or septum. These valves or septa are generally accessed frequently by cannula (such as Luer cannula) or needles to infuse fluid or medication. Upon removal of the accessing cannula from the valve or septum there is commonly a slight negative pressure induced within the catheter which can draw small volume or blood into the catheter tip thereby inducing clotting. Such clot formation increases the infection risk, may induce propagation of thrombosis in the vein, and reduces the useful life of the catheter due to occlusion. U.S. Pat. No. 5,474,544 of the present inventor (the disclosure of which is incorporated by reference as if completely disclosed herein) shows a valve for inducing positive pressure upon withdrawal of a Luer cannula. Subsequently a variety of other positive pressure valves have since been introduced to solve this problem. These valves, especially those introduced subsequent to the issuance of my aforementioned patent, are complex and expensive. In addition, many of the recent positive pressure valves, in association with the increased mechanical complexity of the catheter hub, may add to the colonization risk of the catheter hub. Indeed the catheter hub region is an area which has been increasingly implicated as the source of potentially fatal bacteremia in needleless devices by the Center for Disease Control so it is difficult to suggest, in the interest of patient safety that further increases in the mechanical complexity of such hubs is warranted for any purpose. For these reasons these more complex "positive pressure" valves may be simply exchanging one risk (catheter tip thrombosis) with another, more significant risk (catheter related bacteremia). It is important to reduce the mechanical complexity of any interface between the human vascular system and the environment. In addition conventional positive pressure valves add considerable expense.

The present invention solves the problem of terminal negative pressure upon cannula withdrawal by providing a positive pressure generator proximal the valve or septum for inducing sufficient positive pressure in the lumen or fluid path of the catheter so that a sufficient portion of the fluid at the tip of the catheter is forced into the blood vessel after the cannula or needle has been removed from the hub so that any blood in the tip is displaced back into the vessel or is sufficiently diluted such that clotting within the lumen adjacent the tip is substantially mitigated. The positive pressure generator is preferably comprised of a flexible tube or cavity which has a variable internal volume and which is configured to have a first stable configuration with a first internal fluid volume and a second stable configuration with a smaller internal fluid volume. The tube is configured such that it may be distorted, compressed, or flexed to decrease the volume within the tube during the change from the first configuration to the second configuration thereby forcing at least a portion of the volume of the fluid toward the lumen of the catheter. In one embodiment the tube is pleated with the pleats separated in a first configuration and advanced to intussusept each other in a second configuration the advancement inducing a reduction of the internal volume to cause fluid to flow toward the catheter lumen. In the presently preferred embodiment the a configuration changing member is provided about the tube. The member is preferably movable from a first position wherein the tube is in the first configuration to a second position wherein the tube is distorted into the second configuration. The member is preferably a clamp having opposing surfaces for compressing the tube along a length of the tube sufficient to induce a sufficient flow of fluid within the lumen of the tube toward the catheter lumen to cause displacement of blood out of the tip of the catheter, and further is preferably a peristaltic clamp sized and configured to be mounted with the tubing intermediate the catheter and the hub which can be a elongated slit clamp. The clamp is preferably comprised of resilient and flexible plastic and can include a lock for holding the clamp in the second position with the tube in the compressed position. In the preferred embodiment the clamp is configured to close so as to compress the more proximal portion of the tube first and then occlude the more distal portion so that fluid is propelled toward the vascular system. In one preferred embodiment the clamp is a peristaltic clamp positioned on the tube to progressively compress the tube toward the vascular system. This clamp includes a proximal portion, which occludes the proximal tubing portion first. Preferably the clamp, in the second position holds the clamped portion of the tube in a stable compressed configuration so that negative pressure cannot develop within the lumen of the tube. Alternatively the clamp may be configured to isolate the compressed segment from the proximal valve or septum.

It is the purpose of the present invention to provide a simple and inexpensive flow generator, which can flush blood from the lumen of a catheter and eliminate the need for complex positive pressure generating needleless valves at the hub.

It is further the purpose of the present invention to provide a method for flushing blood from the catheter tip which does not require modification of the needleless valve at the hub.

It is the purpose of the present invention to provide flow generator and method of generating flow which provides a closed fluid filled conduit system having a closed hub at one end and a catheter having an internal lumen extending to a opening at another end, the system having a first stable configuration defining a first internal volume and a second stable configuration defining a second internal volume, the second volume being sufficiently smaller than the first volume so that fluid is displaced toward the lumen and out the opening so that blood is flushed from the opening to prevent the blood from clotting within the lumen adjacent the opening.

It is further the purpose of the present invention to provide a positive flow generator which is free from contact with a luer tip so that infection risk can be reduced.

It is the further the purpose of the present invention to provide a catheter, and a closed hub, and a flexible cavity or tube intermediate the hub and the catheter, and a biasing member for biasing the tube or cavity into a configuration with a reduced volume thereby displacing fluid sufficient fluid into the catheter to flush blood from the distal end of the catheter lumen, the biasing member being free from direct contact with the fluid within the cavity or tubing so that the risk of contact contamination is reduced.

It is the further the purpose of the present invention to provide a catheter, a closed hub, a flexible tube intermediate the hub, and a clamp configured to compress a sufficient length of the tube to displace blood from the catheter lumen to prevent thrombosis within the lumen without inducing substantial negative pressure adjacent the hub.

BRIEF DESCRIPTION OF THE DRAWINGS

These, as well as other objects and advantages of this invention, will be more completely understood and appreciated by careful study of the following more detailed description of the presently preferred exemplary embodiments of the invention taken in conjunction with the accompanying drawings, in which.

DESCRIPTION OF THE PRESENTLY PREFERRED EMBODIMENT

Figure 1:
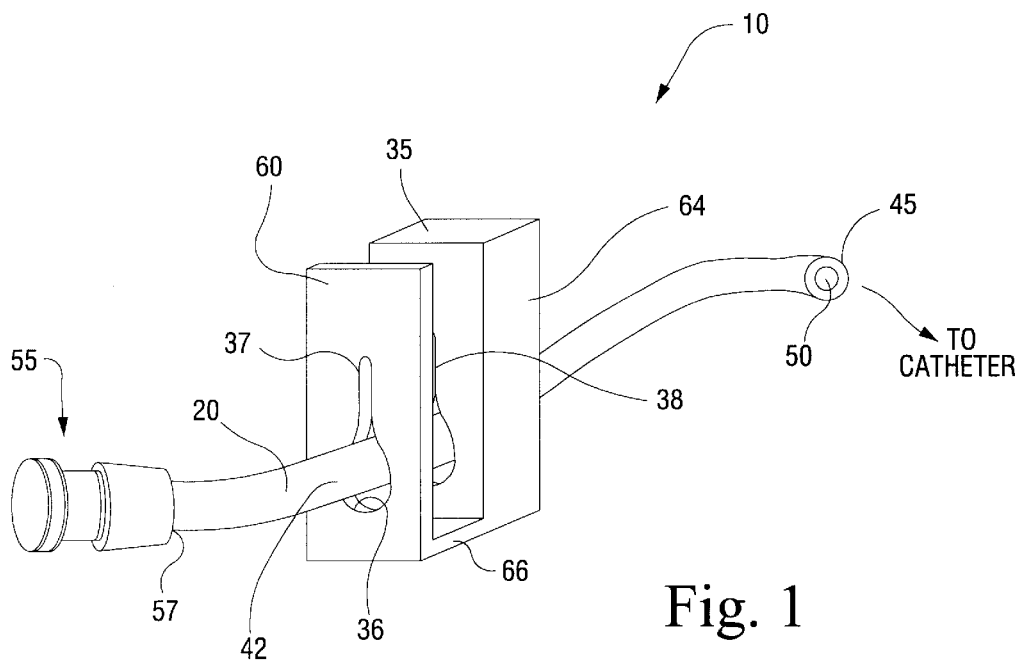
FIG. 1 is a perspective view of a presently preferred embodiment of a positive pressure generator according to the present invention

As shown in FIG. 1, one preferred embodiment of the positive flow generator 10 includes generally a main tube 20 and an elongated positive pressure generating slit clamp 35 having a large opening 36 for receiving the tube 20 and a narrow slit opening 37 for compressing the tube when the tube is advanced into the narrow opening. The tube 20 can be the proximal conventional tubing segment provided with a multilumen catheter 40 or convention IV tubing and can include an enlarged proximal portion 42 having a greater internal volume to increase the amount of positive pressure flush generated by the positive pressure generating clamp 35. The tubing 20 has flexible walls 45 and an internal lumen 50 connected to a hub 55 with an occluding septum 55 at a proximal end 57 and a catheter 40 at a distal end. The catheter 40 has an internal catheter lumen extending to adjacent the tip 42 of the catheter 40. The slit clamp 35 is provided for mounting with the tube 20. The clamp 35 is comprised of flexible plastic such a polypropylene and includes a progressively narrowing slit 37 for compressing the tube 20. In the embodiment of FIG. 1 the clamp includes a first portion 60 having a first slit 37 for occluding the more proximal portion of the tube 20 first and then a second portion 64 having a second slit 38 for squeezing fluid toward the tip of the catheter 40. These portions are connected by a flexible floor 66 to allow each to be advanced over the tube 20 separately. In operation, the proximal portion 60 is advanced to push the tube 20 into the slit 37 so that the more proximal portion 42 of the tube is compressed first to isolate the hub 55 from the more distal tubing 70 the more distal portion 64 of the slit clamp 35 is the advanced so that the tube 20 is compressed by the slit 38 thereby pressing or squeezing fluid toward the catheter 40 to flush any blood which may have invaded the tip 42 of catheter 40 in association with access of the hub 55. In the preferred embodiment, the wall thickness of the proximal portion 60 can be 1–2 mm and the of the distal portion 64 can be 5–10 mm although different sizes may be used. The distal and proximal portions are preferentially separated by a distance of a 3–5 mm for example if the tube 20 is a conventional IV tube having an outside diameter of 4 mm.

Figure 2:
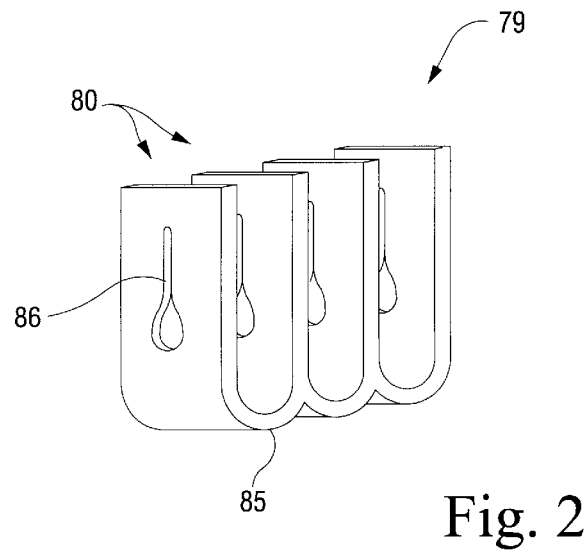
FIG. 2 is a perspective view of another presently preferred embodiment of positive pressure generator according to the present invention
Figure 3:
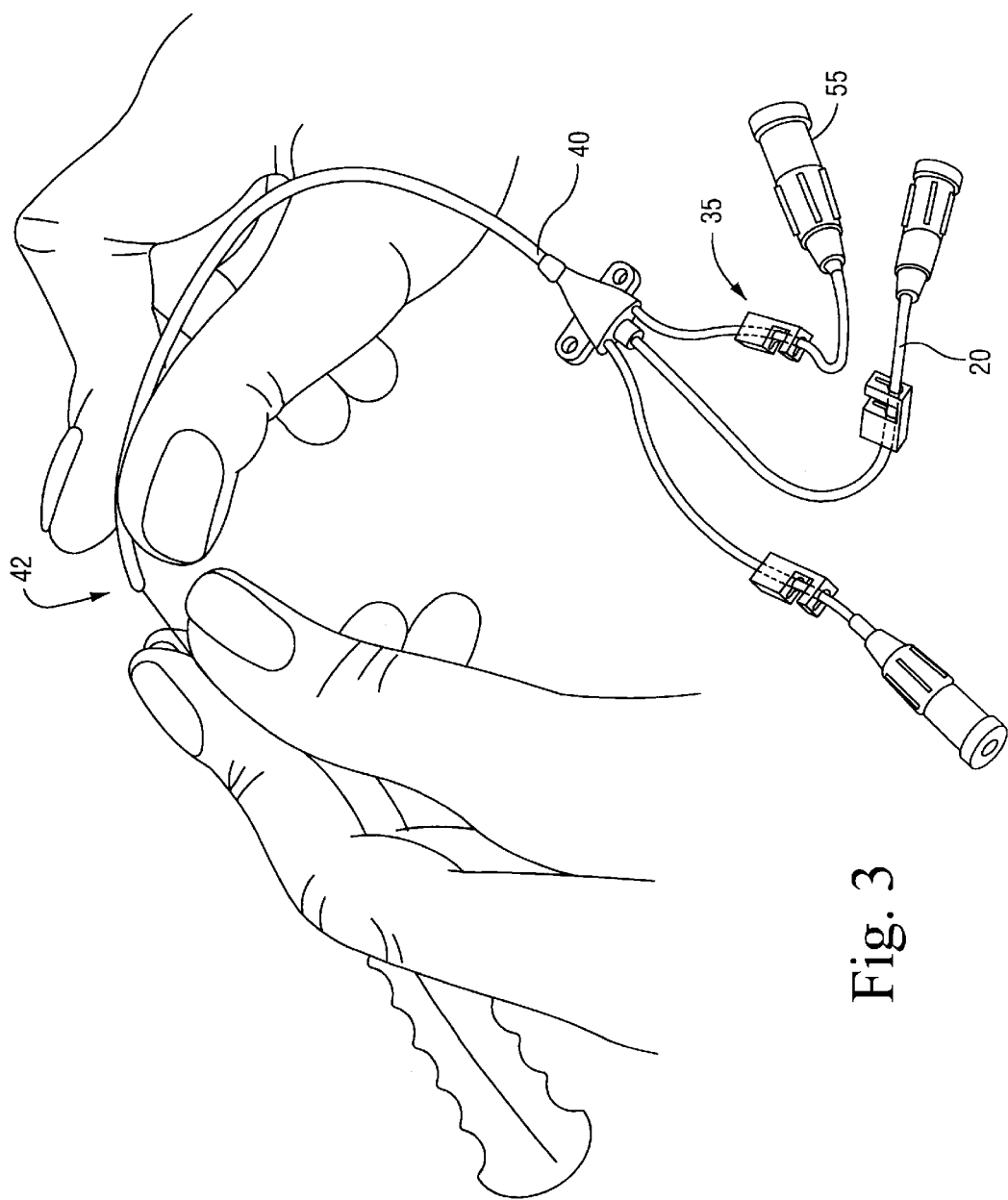
FIG. 3 is a perspective view of a multilumen catheter having positive pressure generating clamps mounted to the multiple pigtail tubing segments.

In an alternative embodiment, shown in FIG. 2 the slit valve 79 can be comprised of multiple narrow separated narrow slit clamps 80 which may be connected as by a flexible bottom connecting mamber 85 so that each can be closed in sequence from the more proximal to the more distal (Which can be performed in one sequential movement of the thumb). This allows very easy and predictable advancement of the clamp into the sequential slits 86 because of the limited direct length of contact between the slits 86 and the tube 20. The wall thickness of clamps 80 can each be approximately 1–2 mm in width and can be separated by 2–3 mm if convention IV tubing having an outside diameter of about 4 mm is used. The closeness of the separation results in the maintenance of compression of the tube 20 intermediate the individual clamps 80 thereby increasing the volume pressed toward the catheter in relation to the actual length of the tube 20 directly contacted by the sequential slits 86. This configuration will result in sufficient fluid displacement to flush blood from the tip, which has entered the tip upon withdrawal of a cannula or luer tip from a conventional needleless hub (such as an Interlink hub of the type shown in WO 90/11103). To provide sufficient flush toward the catheter for substantially all conventional needleless hubs, it is preferable to compress a length of tubing of about 7–12 mm if such convention tubing is used. If preferred the individual slit clamps can be configured in a stair-step configuration with the upper ends of the more proximal slit clamps being higher (not shown) to facilitate the advancement of the more proximal clamp and then each more distal clamp in an easy and predictable sequence by pushing the highest clamps first. Also the flexible connecting member 85 can be narrow flexible struts or pleated supports on the sides or upper surface instead of or in addition to the bottom surface.

Many alternative positive pressure generators can be developed for this purpose using the teachings of this disclosure. For example, a clamp type valve can be used which provides an elongated surface for progressively clamping a more proximal tubing segment toward the catheter and including a locking mechanism for holding the clamp shut with the length of tubing compressed within the clamp. This type of clamp can be, for example, a one piece locking pincer clamp, of the type which are in wide use for hemodialysis bloodlines and for central venous dialysis catheters, but with the pointed pincers modified and flattened to provide the elongated tube compressing surface. The hub of the tube or catheter could be made so that it has a large lumen or cavity which is easily compressed and a clamp or other biasing member can be provided to bias this lumen or cavity into a state of smaller volume as, for example, by compression of the outer wall of the cavity.

Thus, while the invention has been described in connection with what is presently considered to be the most practical and preferred embodiment, it is to be understood that the invention is not to be limited to the disclosed embodiment, but on the contrary, is intended to cover various modifications and equivalent arrangements included within the spirit and scope of the appended claims.

What is claimed is:

1. A catheter-flushing system for maintaining the patency of the lumen of an indwelling catheter having a indwelling portion beneath the skin of a patient, the system comprising:

a tube in flow communication with said indwelling portion, said tube defining a stable internal volume and having at least one proximal terminal for intermittent flow connection with an external fluid source, said proximal terminal including a seal for promptly sealing said proximal terminal upon disconnection of said source so that at least a portion of the fluid entering said tube through said terminal from said source remains sealed within said tube after said source has been disconnected from said proximal terminal thereby defining a residual volume of flush solution within said tube, at least one volume reducer mounted to said tube, said reducer including at least one occluding member displaceable with respect to said tube from a first position to at least a second position, said at least one occluding member, in said second position, substantially occluding at least a first portion of said tube and further and serially substantially occluding at least a second portion of said tube downstream from said first portion to serially displace a sufficient portion of said residual volume of flush solution toward and into said indwelling portion of said catheter to substantially flush blood from said indwelling portion with said flush solution.

2. The catheter-flushing system of claim 1 further wherein said volume reducer is mounted to an external surface of said tube.

3. The catheter-flushing system of claim 1 wherein said volume reducer is configured to progressively compress said tube from said first portion to said second portion to express said flush solution toward said indwelling portion of said catheter.

4. The catheter-flushing system of claim 1 wherein said volume reducer assembly is a peristaltic clamp mounted external said tube.

5. The catheter-flushing system of claim 1 wherein said at least one occluding member is a slide clamp mounted to said tube.

6. The catheter-flushing system of claim 1 wherein said at least one occluding member includes a compressing member for compressing said tube.

7. The catheter-flushing system of claim 6 wherein said compressing member is elongated.

8. The catheter-flushing system of claim 1 wherein said at least one occluding member comprises a plurality of compressing members provided along said tube.

9. The catheter-flushing system of claim 1 wherein said volume reducer is provided so that said at least one occluding member can first substantially occlude said first portion of said tube and thereafter progressively compress said tube toward said catheter so that negative pressure does not develop within said tube intermediate said proximal terminal and said volume reducer.

10. The catheter-flushing system of claim 1 wherein said proximal terminal is a swabbable luer-receiving valve.

11. The catheter-flushing system of claim 1 wherein said proximal terminal includes a self-sealing septum for penetration by a blunt cannula.

12. The catheter-flushing system of claim 1 wherein said tube defines at least one internal dimension, said occluding member being elongated and sized to compress a predetermined length of said tube, said predetermined length and said internal dimension being sufficient such that compression of said predetermined length displaces a sufficient volume of flush solution to flush said indwelling portion of said catheter.

13. The system of claim 12 wherein said tube includes an enlarged portion having an increased internal dimension adjacent said occluding member so that a correspondingly enlarged volume is propelled toward said catheter when said occluding member is moved to said second position.

14. The catheter-flushing system of claim 1 wherein said volume reducer progressively compresses a portion of said tube along a length of greater than 7 millimeters.

15. The catheter-flushing system of claim 1 wherein said volume reducer progressively compresses a portion of said tube along a length of about 7 millimeters–12 millimeters.

16. The catheter-flushing system of claim 1 wherein said volume reducer is configured to selectively at least substantially occlude said first, upstream portion of said tube and further configured to thereafter and sequentially substantially occlude said second, downstream portion of said tube between said substantially occluded first portion and said catheter while holding said first portion in said substantially occluded state.

17. The system of claim 1 wherein said at least one occluding member is a clamp mounted to said tube.

18. The system of claim 17 wherein said clamp is a clamp with an elongated compressing surface.

19. The system of claim 17 wherein said clamp is configured for progressively clamping said tube toward the catheter.

20. The system of claim 1 wherein said volume reducer is comprised of a plurality of compressing members mounted to said tube.

21. The system of claim 19 wherein said plurality of compressing members comprise a plurality of slide clamps serially mounted to said tube.

22. A patient mounted system for providing a bolus flow of a flush solution through an indwelling catheter to flush the lumen of said catheter, the system comprising:

a tube having a distal end connectable to a proximal end of said indwelling catheter and at least one proximal end having a self sealing luer receiving terminal for intermittent connection with a source of flush solution, said terminal including a seal for sealing said proximal end of said tube when said source of flush solution is disconnected from said terminal, said tube further defining an internal space defining a variable internal volume and a lumen extending therethrough from said sealed proximal terminal to said distal end, so that when a source of flush solution is connected to said terminal, flush solution can enter said tube from said source through said terminal and flow through said lumen to at least partially fill said internal space, said lumen defining at least a portion of said internal volume, and a clamp having an elongated compressing surface configured to selectively and progressively propel flush solution through said tube toward said catheter and thereby substantially flush blood from said catheter by progressively reducing said internal volume of said tube after said distal end has been connected with said catheter, said flush solution has been flowed into said space from said source, and said source has been disconnected from said terminal.

23. The system of claim 22 wherein said clamp is a slide clamp.

24. The system of claim 22, wherein said elongated compressing surface of said clamp is configured to substantially occlude a first, upstream portion of said tube and thereafter and sequentially substantially occlude a second portion of said tube, downstream of said first portion.

25. A method for intermittently flushing the lumen of an indwelling catheter with fluid derived from an external fluid source when said catheter is no longer in fluid communication with said external fluid source, the method comprising:

providing a tube defining a stable internal volume and having at least one proximal terminal for intermittent flow connection with said external fluid source, said proximal terminal including a seal for sealing said proximal terminal upon disconnection of said source;

operatively coupling at least one volume reducer to said tube, said reducer including at least one occluding member, displaceable with respect to said tube from a first position to at least a second position, said at least one occluding member, in said second position, substantially occluding at least a first portion of said tube and further substantially occluding at least a second portion of said tube downstream from said first portion;

disposing a distal end of a tube in flow communication with a proximal end of said indwelling catheter;

operatively connecting said external source to said proximal terminal and flowing a flush solution from said external fluid source into said tube to at least partially fill said internal volume;

disconnecting said external fluid source from said proximal terminal, such that at least a portion of said flush solution entering said tube from said source remains within said tube after said source has been disconnected from said proximal terminal, thereby defining a residual volume of flush solution within said tube;

displacing said at least one occluding member from said first position to said second position, to serially and sequentially substantially occlude said first portion of said tube and said second portion of said tube to progressively reduce said internal volume of said tube to serially displace a sufficient portion of said residual volume of flush solution into said catheter to substantially flush said indwelling catheter with said flush solution.

26. A method as in claim 14, wherein said at least one occluding member comprises a plurality of compressing members provided along said tube, and said step of displacing comprises sequentially displacing each said compressing member to substantially occlude a respective portion of said tube, from a proximal most one of said compressing members to a distal most one of said compressing members.

27. A method as in claim 25, wherein said at least one occluding member comprises at least one clamp mounted to said tube, each said clamp having an elongated compression surface configured to first progressively occlude said first, upstream portion of said tube and thereafter and sequentially substantially occlude said second portion of said tube, downstream of said first portion, when the clamp is displaced.

28. A system for intermittently flushing the lumen of an indwelling catheter with fluid derived from an external fluid source when said catheter is no longer in fluid communication with said external fluid source, the system comprising:
a flexible tube defining an axis and further defining a stable internal volume and having at least one proximal terminal for intermittent flow connection with said external fluid source, and a distal terminal for flow connection with said catheter, said proximal terminal including a seal for sealing said proximal terminal upon disconnection of said source;
at least one volume reducer operatively coupled with said tube, said reducer including a plurality of compressing surfaces substantially facing toward each other, said compressing surfaces being elongated and projecting along the axis of the tube, said tube extending along the reducer adjacent the elongated compressing surfaces, at least one of said surfaces being displaceable with respect to said tube from a first position to at least a second position, said opposing surfaces, in said second position, substantially compressing and holding said tube in a compressed state to flush the catheter.

29. The system of claim 28 wherein said opposing compressing surfaces are planer.

30. The system of claim 29 wherein said opposing compressing surfaces are flattened.

31. The system of claim 30 wherein said proximal terminal is a luer receiving valve.

32. The system of claim 21 wherein said surfaces project along said axis to define at least one compression length of said tube adjacent said surfaces, said tube being held in said compressed state substantially said entire compression length when at least one of said surfaces is displaced into said second position.

33. A method for intermittently flushing the lumen of an indwelling catheter with fluid derived from an external fluid source when said catheter is no longer in fluid communication with said external fluid source, the method comprising:
providing a tube defining an axis and further defining a stable internal volume and having at least one proximal terminal for intermittent flow connection with said external fluid source, said proximal terminal including a seal for sealing said proximal terminal upon disconnection of said source;
operatively coupling at least one volume reducer to said tube, said reducer including a plurality of elongated axial compressing surfaces substantially facing toward each other and projecting along the axis of the tube, the tube being disposed adjacent said compressing surfaces, said surfaces defining opposing length, at least one of said surfaces being displaceable with respect to said tube from a first position to at least a second position, said surface, in said second position, substantially compressing and holding in a compressed state said tube substantially along the entire opposing length;
disposing a distal end of a tube in flow communication with a proximal end of said indwelling catheter;
operatively connecting said external source to said proximal terminal and flowing a flush solution from said external fluid source into said tube to at least partially fill said internal volume;
disconnecting said external fluid source from said proximal terminal, such that at least a portion of said flush solution entering said tube from said source remains within said tube after said source has been disconnected from said proximal terminal, thereby defining a residual volume of flush solution within said tube;
displacing said at least one surface from said first position to said second position, to progressively compress said tube and to hold compressed said tube between substantially the entire length of said opposing elongated surfaces to displace a sufficient portion of said residual volume of flush solution into said catheter to substantially flush said indwelling catheter with said flush solution.

34. The method of the claim 33 wherein said surfaces are planer.

35. The method of the claim 33 wherein at least a portion of said both said surfaces are flattened.

* * * * *